United States Patent [19]

Shinohara et al.

[11] Patent Number: 5,142,080
[45] Date of Patent: Aug. 25, 1992

[54] METHOD OF MANUFACTURING DIETHYLAMINOTRIMETHYLSILANE

[75] Inventors: Toshio Shinohara, Takasaki; Muneo Kudo, Annaka; Kazuyuki Matsumura, Annaka; Nobuyuki Suzuki, Annaka, all of Japan

[73] Assignee: Shin-Etsu Chemical Company, Limited, Tokyo, Japan

[21] Appl. No.: 788,156

[22] Filed: Nov. 7, 1991

[30] Foreign Application Priority Data

Nov. 7, 1990 [JP] Japan .................................. 2-302908

[51] Int. Cl.$^5$ ................................................. C07F 7/10
[52] U.S. Cl. ..................................................... 556/410
[58] Field of Search ........................................... 556/410

[56] References Cited

U.S. PATENT DOCUMENTS

| | | | |
|---|---|---|---|
| 3,622,529 | 11/1971 | Evans | 556/410 X |
| 3,646,084 | 2/1972 | Evans et al. | 556/410 |
| 3,665,026 | 5/1972 | Evans | 556/410 |
| 4,474,975 | 10/1984 | Clemons et al. | 556/410 |

Primary Examiner—Paul F. Shaver
Attorney, Agent, or Firm—Millen, White & Zelano

[57] ABSTRACT

Highly pure diethylaminotrimethylsilane can be manufactured in a high yield through the reaction between diethylamine and an N,O-bis(trimethylsilyl)acetamide represented by the following general formula:

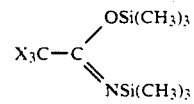

wherein X represents H or F.

8 Claims, No Drawings

METHOD OF MANUFACTURING DIETHYLAMINOTRIMETHYLSILANE

FIELD OF THE INVENTION

This invention relates to a method of manufacturing a diethylaminotrimethylsilane and, more particularly, to a method of manufacturing a highly pure diethylaminotrimethylsilane.

BACKGROUND OF THE INVENTION

Hitherto, diethylaminotrimethylsilane has been manufactured using a known method in which trimethylchlorosilane is allowed to react with diethylamine in the presence of a basic substance such as an amine, as shown by the following reaction scheme (1):

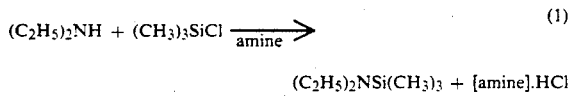

$$(C_2H_5)_2NH + (CH_3)_3SiCl \xrightarrow{amine} (C_2H_5)_2NSi(CH_3)_3 + [amine]\cdot HCl \quad (1)$$

According to this method, hydrochloric acid yielded as a by-product is neutralized and removed in the form of a salt, such as an amine hydrochloride, with the aid of the basic substance (an amine) present in the reaction system. However, the disposal of the foregoing amine hydrochloride in an industrial scale was not easy.

Also, it was difficult to remove such a salt as an amine hydrochloride contained as impurity in the intended product of diethylaminotrimethylsilane, so that the manufactured diethylam inotrimethylsilane was contaminated with quite a bit of chlorine ion. As a result, the above-described method had a serious defect that it was impossible to use the product for electronics materials which have achieved remarkable advancement in recent years.

Therefore, it was desired to find some substitute for the above-described method, which enabled the production of highly pure diethylaminotrimethylsilane.

As a result of our intensive studies for solving the foregoing problem, it has now been found that a diethylaminotrimethylsilane can be manufactured without contaminated by any trace of chlorine ion by the reaction of diethylamine with an N,O-bis(trimethylsilyl)acetamide and, what is more, the by-products yielded in said reaction can be reused, thus achieving this invention.

SUMMARY OF THE INVENTION

A first object of this invention is to provide a novel method of manufacturing a diethylaminotrimethylsilane absolutely free from chlorine ion.

A second object of this invention is to provide a novel method of manufacturing a diethylaminotrimethylsilane wherein it is possible to reuse a by-product.

The above-described objects are attained by a method of manufacturing a diethylaminotrimethylsilane wherein diethylamine is made to react with a N,O-bis(trimethylsilyl)acetamide represented by the following general formula:

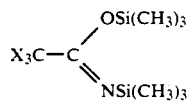

wherein X represents H or F.

DETAILED DESCRIPTION OF THE INVENTION

The reaction adopted in the manufacturing method of this invention is described below in detail.

The N,O-bis(trimethylsilyl)acetamide is added in an amount of 1 to 2 equivalents, preferably 1.1 to 1.4 equivalents, to diethylamine, and undergoes the reaction with diethylamine at a temperature from 20° to 100° C., preferably from 20° to 60° C.

The foregoing reaction may be performed in the presence of a solvent, if needed. Suitable examples of such a solvent include those of hydrocarbon type, such as benzene, n-hexane, cyclohexane, etc., and those of ether type, such as tetrahydrofuran, dioxane, etc. However, solvents usable therein should not be construed as being limited to these examples.

In the reaction of this invention, N-trimethylsilylacetamide (when X is H in the foregoing general formula) or N-trimethylsilyltrifluoroacetamide (when X is F therein) is produced as a by-product. These compounds can be easily converted to N,O-bis(trimethylsilyl) acetamide or N,O-bis(trimethylsilyl)trifluoroacetamide, respectively. Accordingly, these by-products can be reused to avoid not only a disposal problem but also a waste of resources.

In accordance with this invention, therefore, diethylaminotrimethylsilane with extremely high purity can be manufactured since no chlorine is contained in the starting materials. As a result, it becomes possible to use the manufactured diethylaminotrimethylsilane for electronics materials including a primer for photoresists. In addition, there is no waste in this method since the by-products yielded can be reused for the starting material.

EXAMPLES

This invention will now be illustrated in more detail by reference to the following examples. However, the invention should not be construed as being limited to these examples.

EXAMPLE 1

In a 500 ml four-neck flask equipped with a stirrer, a reflux condenser, a dropping funnel and a thermometer, 290.3 g (1.43 mol) of N,O-bis(trimethylsilyl)acetamide was placed, and thereto was added dropwise 94.9 g (1.3 mol) of diethylamine from the dropping funnel over a 1-hour period. During the addition, the temperature of the reaction system was kept within the range of 20° C. to 60° C. to make the reaction be proceeding. At the conclusion of the addition, the temperature was raised to 50–60° C. and kept there for 2 hours, whereby the reaction was matured. Then, the reaction product was subjected to vacuum distillation. As the result of this procedure, 152 g of diethylaminotrimethylsilane was obtained as a fraction having a boiling point of 60° C. under the pressure of 80 mmHg. The yield was 90%.

The diethylaminotrimethylsilane as the foregoing fraction was examined for chlorine concentration (using a measuring instrument, Automatic Titrator GT-05, made by MITSUBISHI CHEMICAL IND. LTD.). The chlorine was not detected.

EXAMPLE 2

185 g of diethylaminotrimethylsilane was prepared in the same manner as in Example 1, except that 94.4 g (1.3 mol) of diethylamine was placed in the same flask as used in Example 1 and 340.4 g (1.4 mol) of N,O-bis(-trimethylsilyl)trifluoroacetamide was added dropwise from the dropping funnel. The yield was 98%, and the chlorine was not detected.

COMPARATIVE EXAMPLE 1

In a 1 liter four-neck flask equipped with a stirrer, a reflux condenser, a dropping funnel and a thermometer were placed 108.5 g (1.0 mol) of trimethylchlorosilane, 111.1 g (1.1 mol) of triethylamine and 300 ml of hexane. Thereto, 73.0 g (1.0 mol) of diethylamine was added dropwise from the dropping funnel over a 1-hour period. During the addition, the temperature of the reaction system was kept within the range of 20° C. to 60° C. to make the reaction be proceeding. At the conclusion of the addition, the temperature was raised to 50-60° C. and kept there for 2 hours, whereby the reaction was matured. Then, the reaction mixture was filtered through a glass filter to remove the salt yielded as a by-product. The filtrate was allowed to stand for one day at room temperature to precipitate the salt. The salt precipitated was filtered off, and the filtrate was subjected to distillation under ordinary pressure to obtain 136.3 g of diethylaminotrimethylsilane as a fraction having a boiling point of 125-126° C. The yield was 94%, and the chlorine concentration was 146 ppm.

From the results obtained in the foregoing examples and comparative example, it has proved that thechlorine contamination in the diethylaminotrimethylsilane obtained in accordance with this invention is incommensurably less than that in the diethylaminotrimethylsilane produced by the conventional method.

What is claimed is:

1. A method of manufacturing a diethylaminotrimethylsilane through the reaction between diethylamine and an N,O-bis(trimethylsilyl) acetamide represented by the following general formula:

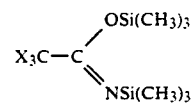

wherein X represents H or F.

2. The method of claim 1, wherein said N,O-bis(-trimethylsilyl) acetamide is used in an amount of 1 to 2 equivalents to diethylamine.

3. The method of claim 2, wherein the amount of the N,O-bis(trimethylsilyl)acetamide used is within the range of 1 to 1.4 equivalents to diethylamine.

4. The method of claim 1, wherein said reaction is carried out at a temperature ranging from 20° C. to 100° C.

5. The method of claim 4, wherein the temperature at which the reaction is carried out is within the range of 20° C. to 60° C.

6. The method of claim 1, wherein said reaction is carried out in the presence of a solvent.

7. The method of claim 6, wherein said solvent is selected from among hydrocarbons or ethers.

8. The method of claim 7, wherein the solvent used is one or more of a solvent selected from among benzene, n-hexane, cyclohexane, tetrahydrofuran or dioxane.

* * * * *